United States Patent
Lim et al.

(10) Patent No.: US 9,354,196 B2
(45) Date of Patent: May 31, 2016

(54) PARTICULATE MATTER SENSOR UNIT

(71) Applicants: Hyundai Motor Company, Seoul (KR); Kia Motors Corporation, Seoul (KR); SNU R&DB FOUNDATION, Seoul (KR)

(72) Inventors: Sera Lim, Mokpo-si (KR); Jin Ha Lee, Seoul (KR); Kuk-jin Chun, Seoul (KR); Seounghyeon Lee, Goyang-si (KR); Kyoung doug Min, Seoul (KR); Sehwan Kim, Seoul (KR)

(73) Assignees: Hyundai Motor Company, Seoul (KR); Kia Motors Corporation, Seoul (KR); SNU R&DB FOUNDATION, Seoul (KR)

( * ) Notice: Subject to any disclaimer, the term of this patent is extended or adjusted under 35 U.S.C. 154(b) by 236 days.

(21) Appl. No.: 14/099,144

(22) Filed: Dec. 6, 2013

(65) Prior Publication Data

US 2014/0165699 A1    Jun. 19, 2014

(30) Foreign Application Priority Data

Dec. 17, 2012  (KR) .................. 10-2012-0147764

(51) Int. Cl.
  *G01N 27/407*   (2006.01)
  *G01N 15/06*   (2006.01)
  *F01N 13/00*   (2010.01)

(52) U.S. Cl.
  CPC ........... *G01N 27/407* (2013.01); *F01N 13/008* (2013.01); *G01N 15/0656* (2013.01); *F01N 2560/05* (2013.01); *F01N 2560/20* (2013.01)

(58) Field of Classification Search
  CPC ............ G01N 15/0656; G01N 27/407; F01N 2560/05; F01N 2560/20; F01N 13/008
  USPC .................................................. 73/23.31
  See application file for complete search history.

(56) References Cited

U.S. PATENT DOCUMENTS

| | | | | |
|---|---|---|---|---|
| 4,656,832 A * | 4/1987 | Yukihisa | ................ | F01N 3/027 324/717 |
| 7,770,432 B2 * | 8/2010 | Roesch | .............. | G01N 15/0656 73/23.33 |
| 8,182,665 B2 * | 5/2012 | Dorfmueller | ........... | F01N 11/00 204/424 |
| 8,382,884 B2 * | 2/2013 | Okayama | ........... | G01N 15/0656 60/275 |
| 9,134,216 B2 * | 9/2015 | Hedayat | ............. | G01N 15/0656 |
| 2009/0126458 A1 * | 5/2009 | Fleischer | ........... | G01N 15/0656 73/28.01 |

(Continued)

FOREIGN PATENT DOCUMENTS

| | | |
|---|---|---|
| JP | 2005-010083 A | 1/2005 |
| JP | 2011-80781 A | 4/2011 |

(Continued)

*Primary Examiner* — Freddie Kirkland, III
(74) *Attorney, Agent, or Firm* — Morgan, Lewis & Bockius LLP

(57) ABSTRACT

A particulate matter sensor unit including a sensor on one side of an exhaust line and configured to employ an electrostatic induction for generating electric charges by a particulate matter contained in an exhaust gas when the particulate matter passes the sensor. The sensor includes a body portion, an electrode portion formed in a front of the body portion on one side of the front and adjacent to the particulate matter, a heating portion in a rear of the body portion on one side of the rear corresponding to the electrode portion, a power input portion in the rear of the body portion on the other side of the rear and to supply a power to the heating portion, and connection lines to connect the power input portion to the heating portion, which use the supplied power to generate heat for burning and removing the particulate matter.

5 Claims, 9 Drawing Sheets

(56) References Cited

U.S. PATENT DOCUMENTS

| | | | | |
|---|---|---|---|---|
| 2009/0217737 | A1* | 9/2009 | Dorfmueller | F01N 11/00 73/28.01 |
| 2011/0081276 | A1* | 4/2011 | Teranishi | G01N 33/0036 422/83 |
| 2011/0314796 | A1* | 12/2011 | Nakamura | F01N 9/002 60/276 |
| 2013/0145821 | A1* | 6/2013 | Lee | G01N 15/0656 73/23.31 |
| 2014/0116113 | A1* | 5/2014 | Lee | G01N 15/0656 73/28.01 |

FOREIGN PATENT DOCUMENTS

| | | |
|---|---|---|
| JP | 2011-80942 A | 4/2011 |
| JP | 2011-153930 A | 8/2011 |
| JP | 2012-083210 A | 4/2012 |

* cited by examiner

FIG.8

| Substrate Material | Silicon |
|---|---|
| Heating Line Material | Platinum |
| Input Power | 20 W |
| External Temperature | 500 °C |

FIG.9

| Simulation results of heater patterns | Symmetric | Asymmetric 1:1 | Asymmetric 2:1 | Asymmetric 3:1 |
|---|---|---|---|---|
| Heating Area (mm$^2$) | 3.06 | 2.87 | 35.36 | 47.04 |
| Max. Temp. (°C) | 835.5 | 840.35 | 802.55 | 773.87 |
| min Temp.(°C) | 691.77 | 694.09 | 682.39 | 676.62 |
| Uniformity (%) | 6.78 | 6.86 | 5.83 | 4.81 |

PARTICULATE MATTER SENSOR UNIT

CROSS-REFERENCE TO RELATED APPLICATION

The present application claims priority of Korean Patent Application Number 10-2012-0147764 filed Dec. 17, 2012, the entire contents of which application are incorporated herein for all purposes by this reference.

BACKGROUND OF INVENTION

1. Field of Invention

The present invention relates to a particulate matter sensor unit for precisely and effectively sensing damage to a particulate filter configured to filter particulate matter (or an exhaust gas) contained in an exhaust gas and maintaining sensitivity.

2. Description of Related Art

A particulate filter (PF) for reducing an exhaust gas is applied to a vehicle. A differential pressure sensor is used to sense the amount of an exhaust gas collected by the particulate filter.

The particulate filter can be selectively applied to all internal combustion engines, such as a diesel vehicle, a gasoline vehicle, and a gas vehicle.

In use, in accordance with exhaust gas control, the sensing precision of particulate matter collected by a diesel particulate filter by using the existing differential pressure sensor can be lowered, and it is not easy to sense damage to the diesel particulate filter.

Meanwhile, research into a sensor for sensing particulate matter continues to be carried out, and research is also being carried out in order to maintain the sensitivity of a sensor by removing particulate matter when the particulate matter is adhered to the sensor.

The information disclosed in this Background section is only for enhancement of understanding of the general background of the invention and should not be taken as an acknowledgement or any form of suggestion that this information forms the prior art already known to a person skilled in the art.

SUMMARY OF INVENTION

The present invention has been made in an effort to provide a particular matter sensor unit having advantages of precisely sensing the amount of an exhaust gas slipped into the rear part of a particulate filter, precisely sensing the amount of an exhaust gas collected by the particulate filter and whether the particulate filter has been damaged or not based on the amount of the sensed exhaust gas, and easily removing particulate matter adhered to an electrode portion.

A particulate matter sensor unit in accordance with various aspects of the present invention may include a sensor disposed on one side of an exhaust line and configured to employ an electrostatic induction for generating electric charges by a particulate matter contained in an exhaust gas when the particulate matter passes the sensor or flows adjacent to the sensor. The sensor may include a body portion, an electrode portion formed in a front of the body portion on one side of the front and configured to be adjacent to the particulate matter, a heating portion formed in a rear of the body portion on a respective side of the rear corresponding to the electrode portion, a power input portion formed in the rear of the body portion on the other side of the rear and configured to supply a power to the heating portion, and connection lines configured to connect the power input portion to the heating portion, wherein the heating portion uses the supplied power to generate heat for removing the particulate matter adhered to the electrode portion by burning the particulate matter.

The electrode portion may have a furrow or a plurality of furrows extending substantially in a cross direction with respect to a flow direction of the exhaust gas, and the electrode portion may be formed substantially vertically with respect to the flow direction of the exhaust gas.

The heating portion, the connection lines, and the power input portions may be made of a material comprising platinum (Pt). The body portion may be made of a material comprising silicon (Si). The power inputted to the power input portions may be about 15 W to 25 W, and an external temperature of the body portion may be about 150° C. to 700° C. The connection lines configured to connect the heating portion to the power input portion may be formed along the edges of the body portion.

The heating portion may include first heating lines extended from the respective ends of the connection lines in the width direction of the body portion and configured to be adjacent to the center line of the body portion in the length direction of the body portion at both edges of the body portion, second heating lines extended from the respective ends of the first heating lines substantially parallel to the center line and configured to be adjacent to the center line, third heating lines extended from the respective edges of the second heating lines in the width direction of the body portion and configured to be adjacent to both the edges of the body portion, and fourth heating lines extended from the respective edges of the third heating lines along both the edges of the body portion.

The heating portion may have a symmetric shape with respect to the center line in the length direction of the body portion.

The heating portion may include an edge line extended along an edge of the body portion, first heating lines extended from the end of the edge line in a width direction of the body portion and configured to be adjacent to the edge of the body portion on another side of the edge line with respect to the edge of the body portion, second heating lines extended from the respective ends of the first heating lines along the edge of the body portion, third heating lines extended from the respective ends of the second heating lines in the width direction of the body portion and configured to be adjacent to the edge line, and fourth heating lines extended from the respective edges of the third heating lines substantially parallel to the edge line.

Each of the first, the second, the third, and the fourth heating lines may have a predetermined width, and a predetermined gap may be formed between the first, the second, the third, and the fourth heating lines.

The particulate matter sensor unit in accordance with various aspects of the present invention can precisely sense the amount of collected particulate matter, such as an exhaust gas of a Diesel Particulate Filter (DPF), or the amount of particulate matter contained in an exhaust gas and easily removing particulate matter adhered to an electrode portion by heating the adhered particulate matter using a heating portion.

The methods and apparatuses of the present invention have other features and advantages which will be apparent from or are set forth in more detail in the accompanying drawings, which are incorporated herein, and the following Detailed Description, which together serve to explain certain principles of the present invention.

BRIEF DESCRIPTION OF THE DRAWINGS

FIG. 8 is a table showing the characteristics of an exemplary particulate matter sensor in accordance with the present invention.

FIG. 9 is a table showing the experiment results of an exemplary particulate matter sensor in accordance with the present invention.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

In various embodiments of the present invention, an example in which a sensor 120 is applied to a diesel particulate filter is illustrated, but the present invention is not limited thereto. The sensor can be selectively applied to all internal combustion engines that discharge particulate matter, such as a gasoline engine, a gas engine, and a bio engine using bio fuel. Accordingly, the sensor in accordance with various embodiments of the present invention can be changed into and applied to a particulate filter, a diesel particulate filter, and a gasoline particulate filter.

Figure 1:
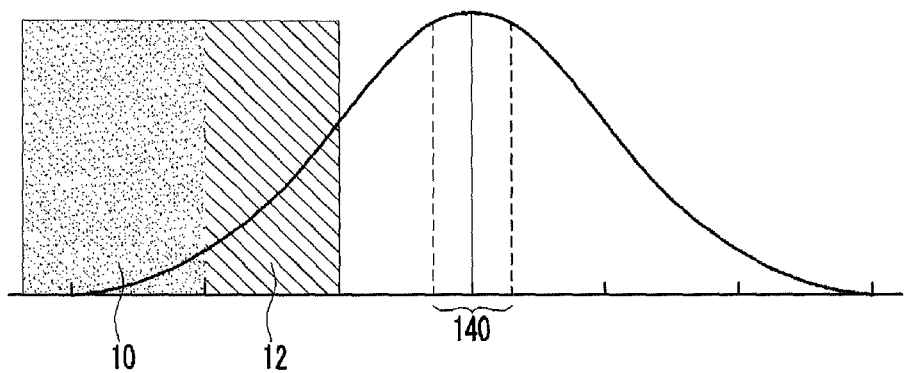
FIG. 1 is a graph showing the amount of particulate matter collected by a diesel particulate filter in relation to differential pressure.
Figure 2:
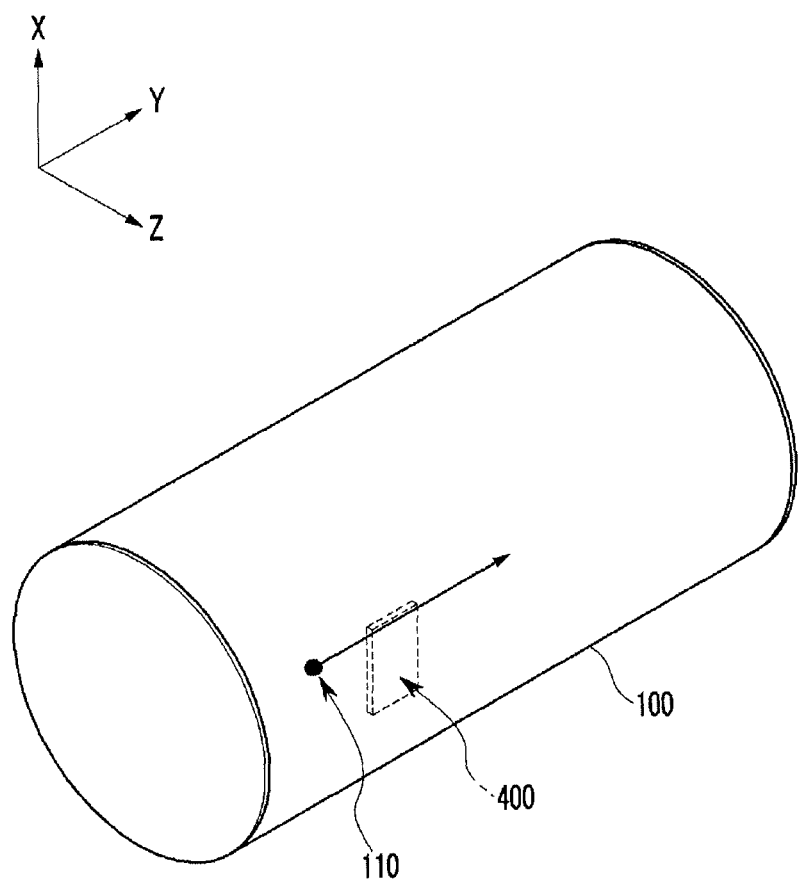
FIG. 2 is a schematic internal perspective view showing a state in which an exemplary particulate matter sensor in accordance with the present invention is disposed in an exhaust line.
Figure 3:
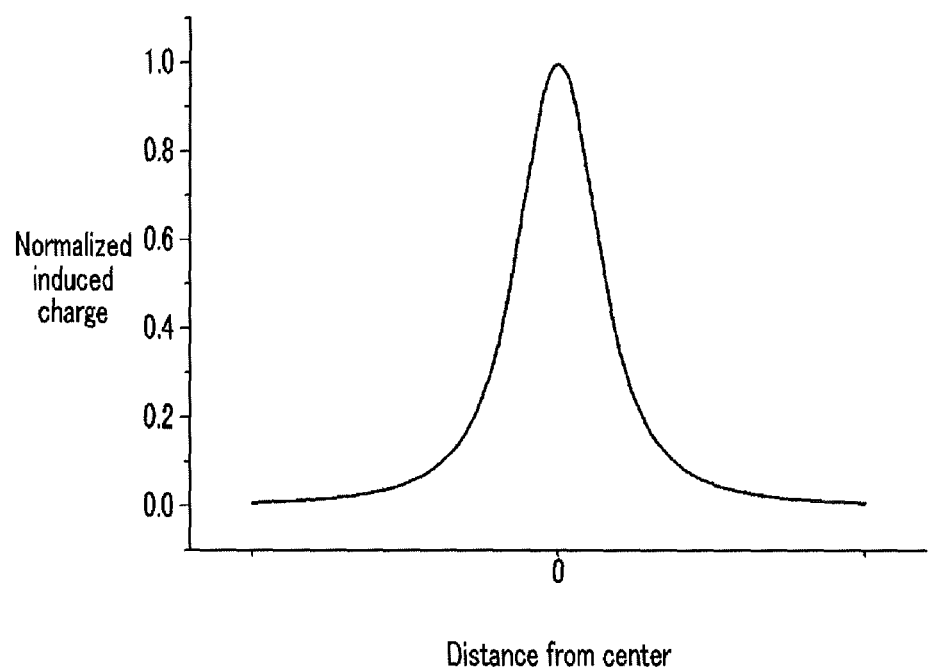
FIG. 3 is a graph showing the amount of electric charges generated from an exemplary sensor unit in relation to a distance between a particulate matter sensor and the particulate matter in accordance with the present invention.
Figure 4:
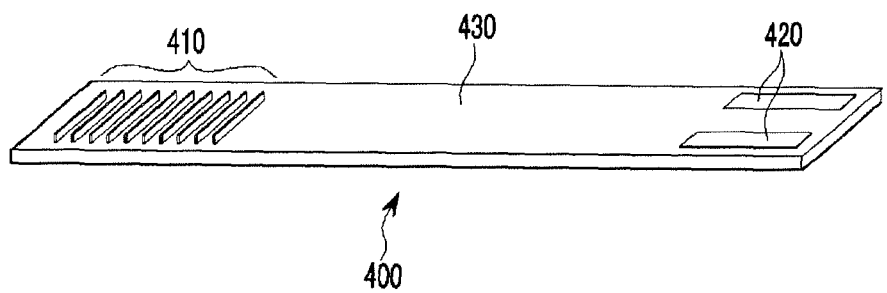
FIG. 4 is a perspective view showing the front of an exemplary particulate matter sensor in accordance with the present invention.

FIG. 1 is a graph showing the amount of particulate matter collected by a diesel particulate filter, FIG. 2 is a schematic internal perspective view showing a state in which a particulate matter sensor is disposed in an exhaust line, FIG. 3 is a graph showing the amount of electric charges generated from a sensor unit in relation to a change of the distance from the particulate matter sensor, and FIG. 4 is a perspective view showing the front of the particulate matter sensor, in accordance with various embodiments of the present invention.

Referring to FIG. 1, a horizontal axis indicates the differential pressure and a vertical axis indicates collection efficiency. A first region 140 substantially in the center of the graph is the differential pressure region of a sensor unit in which collection efficiency of a diesel particulate filter is high, and a second region 12 is a region in which collection efficiency of a diesel particulate filter by a common or existing differential pressure sensor is 50% or less. Furthermore, a third region 10 is a region in which collection efficiency is close to zero (0) because the diesel particulate filter is damaged.

As shown in FIG. 1, the existing differential pressure sensor is problematic in that sensitivity in terms of collection efficiency and differential pressure is low and a sensing region is limited. Accordingly, there is a need for a new type of a differential pressure sensor or a particulate matter sensor.

Referring to FIGS. 2 and 4, an exhaust gas flows within an exhaust line 100, and particulate matter 110 is contained in the exhaust gas. The particulate matter 110 passes close to the electrode portion 410 of a sensor 400 (i.e., a particulate matter sensor).

When the particulate matter 110 passes, the sensor 400 generates a signal. A factor that the signal is generated from the sensor 400 lies in that when charged particulate matter passes, the signal is generated by electric charges induced to the electrode portion 410 of the sensor 400.

FIG. 3 shows an induced charge signal graph in relation to a distance x between the sensor 400 and the particulate matter. In general, an electric field generated by charged particles is represented by the following equation:

$$\vec{E} = \frac{Q}{4\pi\varepsilon_0 r^2} \vec{a_r}$$

where Q is the amount of electric charges of the charged particles, and r is a distance from the charged particles. Furthermore, $\varepsilon_o$ is a dielectric constant in vacuum.

Surface charges having the same value as a value of an electric field generated by charged particulate matter at the interface of a sensor electrode are generated in the sensor electrode. The induced charges can be solved by Laplace's equation. Assuming that charged dot charges having the amount of electric charges of a Q value in related to a flat conductor plate that is placed on a plane in which z is zero (0) in an orthogonal coordinate system are placed at (0,0,d), potential generated by the dot charges and the density of surface charges induced by the dot charges can be represented by the following equations.

For the potential generated by the dot charges:

$$V(x, y, z) = \frac{Q}{4\pi\varepsilon_0} \left[ \frac{1}{\sqrt{x^2 + y^2 + (z-d)^2}} - \frac{1}{\sqrt{x^2 + y^2 + (z+d)^2}} \right]$$

For the electric field generated by the dot charges:

$$\vec{E} = -\nabla V$$
$$= \frac{Q}{4\pi\varepsilon_0} \left[ \frac{x \cdot \overline{a_x} + y \cdot \overline{a_y} + (z-d) \cdot \overline{a_z}}{(x^2 + y^2 + (z-d)^2)^{3/2}} - \frac{x \cdot \overline{a_x} + y \cdot \overline{a_y} + (z+d) \cdot \overline{a_z}}{(x^2 + y^2 + (z+d)^2)^{3/2}} \right]$$

For the density of induced surface charges:

$$\rho_s = \varepsilon_0 E_z \big|_{z=0}$$
$$= -\frac{Qd}{2\pi(x^2 + y^2 + d^2)^{3/2}}$$

where $\bar{a}_x$, $\bar{a}_y$, $\bar{a}_z$ where indicate respective unit vectors in the x, y, and z-axis directions in the orthogonal coordinate system.

If the amount of electric charges induced into the sensing electrode by the charged particles in relation to the distance x is represented by a graph, a signal having a pulse form is generated as shown in FIG. 3 according to a change in the distance between the charged particles and the sensing electrode.

Referring to FIG. 4, the sensor 400 includes a body portion 430, the electrode portion 410 formed in the front of the body portion 430 on one side of the front, and power connection portions 420 formed in the front of the body portion 430 on the other side of the front. When particulate matter contained in an exhaust gas passes close to the electrode portion 410, electric charges are generated and then transferred to an external control unit through the power connection portions 420.

Figure 5:
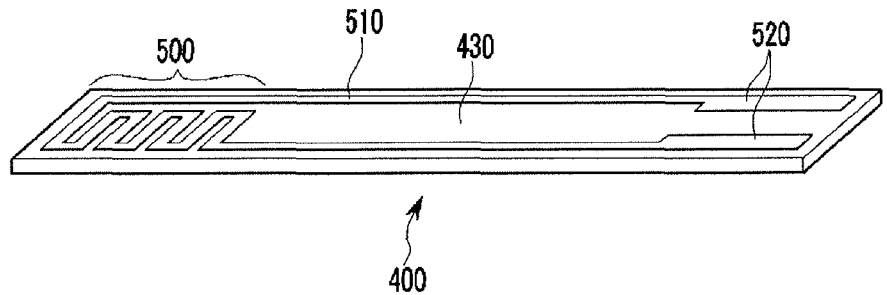
FIG. 5 is a perspective view showing the rear of an exemplary particulate matter sensor in accordance with the present invention.

FIG. 5 is a perspective view showing the rear of the particulate matter sensor in accordance with various embodiments of the present invention. Referring to FIG. 5, the sensor 400 includes the body portion 430, a heating portion 500 formed in the rear of the body portion 430 on one side of the rear, and power input portion or portions 520 formed in the rear of the body portion 430 on the other side of the rear. Furthermore, the heating portion 500 and the power input portions 520 are electrically connected to each other by connection lines 510.

In various embodiments of the present invention, the body portion 430 contains a silicon (Si) component or is made of a material comprising Si, and the heating portion 500, the connection lines 510, and the power input portions 520 contain a platinum (Pt) component or are made of a material comprising Pt.

Figure 6:
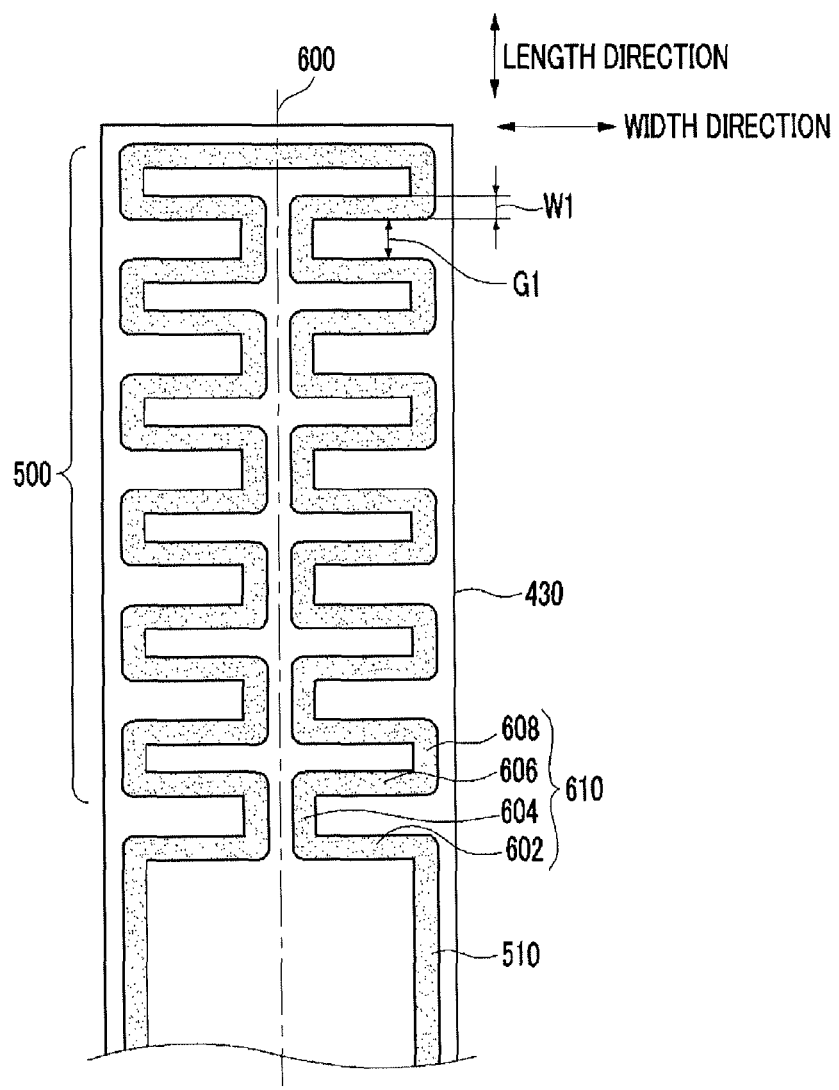
FIG. 6 is a detailed top plan view showing a symmetrical heating portion at the rear of an exemplary particulate matter sensor in accordance with the present invention.

FIG. 6 is a detailed top plan view showing symmetrical heating portion at the rear of the particulate matter sensor in accordance with various embodiments of the present invention. Referring to FIG. 6, the heating portion 500 is formed in the rear of the body portion 430 on one side of the rear, and the connection lines 510 are connected to the heating portion 500.

In some embodiments, the heating portion 500 has a symmetrical form on the basis of a center line 600 in the length direction of the body portion 430. More particularly, in some embodiments, the heating portion 500 include first heating lines 602 extended from the respective ends of the connection lines 510 in the width direction of the body portion 430 and configured to be adjacent to the center line 600 of the body portion 430 in the length direction of the body portion 430 at both edges of the body portion 430, second heating lines 604 extended from the respective ends of the first heating lines 602 in parallel to the center line 600 and configured to be adjacent to the center line 600, third heating lines 606 extended from the respective edges of the second heating lines 604 in the width direction of the body portion 430 and configured to be adjacent to both the edges of the body portion 430, and fourth heating lines 608 extended from the respective edges of the third heating lines 604 along both the edges of the body portion 430.

Each of the first, the second, the third, and the fourth heating lines 602, 604, 606, and 608 of the heating portion 500 has a predetermined width W1, and a predetermined gap G1 is formed between the first, the second, the third, and the fourth heating lines. The width and gap can be varied depending on design specifications.

Figure 7:
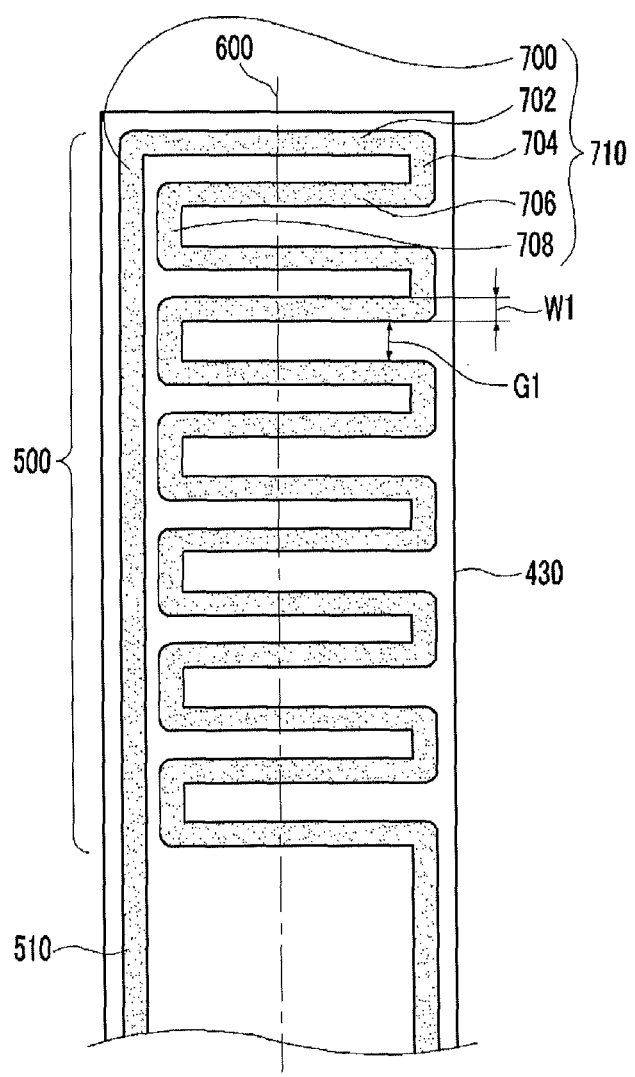
FIG. 7 is a detailed top plan view showing an asymmetrical heating portion at the rear of an exemplary particulate matter sensor in accordance with the present invention.

FIG. 7 is a detailed top plan view showing an asymmetrical heating portion at the rear of the particulate matter sensor in accordance with various embodiments of the present invention. In some embodiments, the heating portion 500 has an asymmetrical form on the basis of the center line 600 in the length direction of the body portion 430.

More particularly, in some embodiments, the heating portion 500 includes an edge line 700 extended along an edge of the body portion 430, first heating lines 702 extended from the end of the edge line 700 in the width direction of the body portion 430 and configured to be adjacent to an edge of the body portion 430 on the other side of the edge line 700, second heating lines 704 extended from the respective ends of the first heating lines 702 along an edge of the body portion 430, third heating lines 706 extended from the respective ends of the second heating lines 704 in the width direction of the body portion 430 and configured to be adjacent to the edge line 700, and fourth heating lines 708 extended from the respective edges of the third heating lines 706 in parallel to the edge line 700.

Each of the first, the second, the third, the fourth, and the fifth heating lines 702, 704, 706, and 708 of the heating portion 500 has a predetermined width W1, and a predetermined gap G1 is formed between the first, the second, the third, the fourth, and the fifth heating lines. The width and gap can be varied depending on design specifications.

FIG. 8 is a table showing the characteristics of the particulate matter sensor in accordance with various embodiments of the present invention. Referring to FIG. 8, the body portion 430 is made of a silicon material, and the heating portion 500, the connection lines 510, and the power input portions 520 are made of a platinum material.

A power source inputted to the power input portions 520 can be set to 20 W or about 15 W to 25 W, which can be readily varied depending on design specifications. Furthermore, temperature of an exhaust gas near the electrode portion 410 can be set to 500° C., and the temperature of the exhaust gas can vary in a range of about 150° C. to 700° C.

FIG. 9 is a table showing the experiment results of the particulate matter sensor in accordance with various embodiments of the present invention. In FIG. 9, max. Temp. is a maximum temperature, min Temp. is a minimum temperature, and uniformity is the uniformity of temperature. Symmetric indicates that the heating portion 500 has a symmetrical line type, asymmetric 1:1 indicates a case where a ratio of the gap and width of the line is 1:1, asymmetric 2:1 indicates a case where a ratio of the gap and width of the line is 2:1, and asymmetric 3:1 indicates a case where a ratio of the gap and width of the line is 3:1.

In various embodiments of the present invention, when the electrode portion 410 has a furrow type, the sensor is for removing particulate matter within the furrows of the electrode portion 410 by burning the particulate matter and can easily remove the particulate matter by burning the particulate matter at 650° C. As shown in FIG. 9, a minimum temperature of the heating portion 500 exceeds 650° C.

For convenience in explanation and accurate definition in the appended claims, the terms "front" or "rear", and etc. are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present inven-

What is claimed is:

1. A particulate matter sensor unit, comprising:
 a sensor disposed on one side of an exhaust line and configured to employ an electrostatic induction for generating electric charges by a particulate matter contained in an exhaust gas when the particulate matter passes the sensor or flows adjacent to the sensor, wherein the sensor comprises:
 a body portion;
 an electrode portion formed in a front of the body portion on one side of the front and configured to be adjacent to the particulate matter;
 a heating portion formed in a rear of the body portion on a respective side of the rear corresponding to the electrode portion;
 a power input portion formed in the rear of the body portion on the other side of the rear and configured to supply a power to the heating portion; and
 connection lines configured to connect the power input portion to the heating portion,
 wherein the heating portion uses the supplied power to generate heat for removing the particulate matter adhered to the electrode portion by burning the particulate matter,
 wherein the electrode portion has a furrow or a plurality of furrows extending substantially in a cross direction with respect to a flow direction of the exhaust gas, and the electrode portion is formed substantially vertically with respect to the flow direction of the exhaust gas,
 wherein the connection lines configured to connect the heating portion to the power input portion are formed along edges of the body portion,
 wherein the heating portion comprises:
  first heating lines extended from respective ends of the connection lines in a width direction of the body portion and configured to be adjacent to a center line of the body portion in a length direction of the body portion at both edges of the body portion;
  second heating lines extended from respective ends of the first heating lines substantially parallel to the center line and configured to be adjacent to the center line;
  third heating lines extended from respective edges of the second heating lines in the width direction of the body portion and configured to be adjacent to both the edges of the body portion; and
  fourth heating lines extended from respective edges of the third heating lines along both the edges of the body portion,
 wherein the heating portion has a symmetric shape with respect to the center line in the length direction of the body portion.

2. The particulate matter sensor unit of claim 1, wherein the heating portion, the connection lines, and/or the power input portion are made of a material comprising platinum (Pt).

3. The particulate matter sensor unit of claim 1, wherein the body portion is made of a material comprising silicon (Si).

4. The particulate matter sensor unit of claim 1, wherein the power inputted to the power input portion is about 15 W to 25 W, and an external temperature of the body portion is about 150 ° C. to 700 ° C.

5. The particulate matter sensor unit of claim 1, wherein each of the first, the second, the third, and the fourth heating lines has a predetermined width, and a predetermined gap is formed between the first, the second, the third, and the fourth heating lines.

* * * * *